(12) United States Patent
Chen et al.

(10) Patent No.: US 12,191,725 B2
(45) Date of Patent: Jan. 7, 2025

(54) ROTATING MAGNETIC FIELD-VARIABLE PYRAMID ENERGY CABIN

(71) Applicants: Chong Chen, Xi'an (CN); Haiqin Xu, Xi'an (CN); Guanzhu Chen, Xi'an (CN); Ming Yang, Xi'an (CN)

(72) Inventors: Chong Chen, Xi'an (CN); Haiqin Xu, Xi'an (CN); Guanzhu Chen, Xi'an (CN); Ming Yang, Xi'an (CN)

(73) Assignee: XI'AN XIAOCAO HERBAL TECHNOLOGY CO., LTD., Xi'an (CN)

( * ) Notice: Subject to any disclaimer, the term of this patent is extended or adjusted under 35 U.S.C. 154(b) by 281 days.

(21) Appl. No.: 18/064,266

(22) Filed: Dec. 11, 2022

(65) Prior Publication Data
US 2024/0014722 A1    Jan. 11, 2024

(30) Foreign Application Priority Data

Jul. 8, 2022   (CN) .......................... 202210801625.2
Jul. 8, 2022   (CN) .......................... 202221769899.X (51) Int. Cl.
*H02K 21/14*    (2006.01)
*H01F 7/02*    (2006.01)
*H02K 21/24*    (2006.01)

(52) U.S. Cl.
CPC ............. *H02K 21/14* (2013.01); *H02K 21/24* (2013.01); *H01F 7/02* (2013.01)

(58) Field of Classification Search
CPC .......... H02K 21/24; H02K 21/14; A61N 2/02; A61N 2/06; A61N 2/12; H01F 7/02; H01F 7/202; H01F 6/06
USPC ...................................................... 310/156.01
See application file for complete search history.

(56) References Cited

U.S. PATENT DOCUMENTS

| | | | |
|---|---|---|---|
| 4,726,046 A * | 2/1988 | Nunan ................ | A61N 5/1081 378/65 |
| 7,759,938 B2 * | 7/2010 | Prado .................... | G01N 24/08 324/319 |
| 10,037,841 B2 * | 7/2018 | Suzara ................ | A61B 5/0036 |
| 10,522,277 B1 * | 12/2019 | Honein ................ | H02N 15/04 |
| 2013/0317343 A1 * | 11/2013 | Klimenko ............ | A61B 5/0046 600/3 |
| 2016/0111192 A1 * | 4/2016 | Suzara ..................... | H01F 6/06 335/301 |
| 2018/0340825 A1 * | 11/2018 | Suzara ..................... | G01J 3/42 |
| 2020/0016424 A1 * | 1/2020 | Tofani ................ | A61K 31/282 |

* cited by examiner

*Primary Examiner* — Alex W Mok (57) ABSTRACT

In a rotating magnetic field-variable pyramid energy cabin, shielding plate permanent magnets are disposed on inner surfaces of three triangular shielding plates forming a pyramid shape, to form a stable magnetic field in the triangular shielding plates. A top rotating magnet is disposed at a top of the triangular shielding plates. A bottom rotating magnet is disposed below a seat. The magnetic field in the triangular shielding plates is rotated, to enable a vortex in turbulence of magnetic lines of force to generate a torsion field. The torque of the torsion field changes the spin states of electrons and atomic cores in a hypoxic microfield in the body of a patient, to arrange the electrons and atomic cores in a uniform magnetic field direction. The magnetic actuation of the electrons and atomic cores can make the microfield environment serialized and orderly and increase the negentropy.

10 Claims, 7 Drawing Sheets

FIG. 9

ROTATING MAGNETIC FIELD-VARIABLE PYRAMID ENERGY CABIN

This application claims priority to Chinese Patent Application Nos. CN 202210801625.2, filed on Jul. 8, 2022 and CN 202221769899.X, filed on Jul. 8, 2022, both of which are incorporated by reference for all purposes as if fully set forth herein.

TECHNICAL FIELD

The present invention belongs to the field of machinery, and specifically to a rotating magnetic field-variable pyramid energy cabin.

BACKGROUND

A microenvironment in which cancer cells grow is called a "microfield". In addition to cancer cells, there are immune cells, inflammatory cells, fibroblasts, intercellular matrix, capillaries, and other biomolecules in the microfield. Cancer cells are characterized by high metabolism, rapid growth, and high fertility. Cancer cells have a high energy demand, that is, have higher consumption of sugar and oxygen than normal cells, which makes the microenvironment of cancer cells hypoxic and the pH lower. This phenomenon is called "microfield hypoxia." The phenomenon "microfield hypoxia" causes cancer cells to metastasize and become resistant to conventional chemotherapy and radiotherapy, and is a factor contributing to the treatment failure and poor prognosis of patients with hypoxic tumors.

In a hypoxic microfield, the metabolic energy of cancer cells comes from glycolysis to a large extent. Energy metabolism reactions in oxidative phosphorylation of cells are restored by correcting microfield hypoxia. The amount of sugar and oxygen occupied by cancer cells decreases, the amount of sugar and oxygen received by surrounding immune cells increases, and the activity of immune cells is enhanced. The glycolysis of cancer cells is reduced, the accumulation of lactic acid in intercellular matrix is reduced, the pH of the intercellular matrix becomes larger, and the inhibitory effect on the proliferation of normal cells is diminished.

SUMMARY

An objective of the present invention is to overcome the foregoing deficiencies, and provides a rotating magnetic field-variable pyramid energy cabin, so that a torsion field can be formed in the energy cabin.

To achieve the foregoing objective, the present invention provides a support frame, where the support frame is a cuboid, three triangular shielding plates are disposed on the support frame, bottoms of the triangular shielding plates are disposed on the support frame, adjacent sides of the three triangular shielding plates are connected, the three triangular shielding plates form a pyramid shape, a plurality of shielding plate permanent magnets are disposed on an inner surface of each triangular shielding plate, a top rotating magnet is disposed at a top of the three triangular shielding plates, a seat is disposed in the support frame, a bottom rotating magnet is disposed below the seat, the seat is made of a non-magnetically conductive material, and variable electromagnets are disposed on a top frame of the support frame.

The top rotating magnet includes a top motor, a top turntable is disposed on a motor shaft of the top motor, and a plurality of top rotating permanent magnets are disposed on the top turntable.

Four rotating permanent magnets are provided, the four rotating permanent magnets are disposed on the top turntable at equal angles, an S pole of each rotating permanent magnet points at the seat, the rotating permanent magnet is 5 cm away from a rotation center, a total field strength of the four rotating permanent magnets ranges from 0.7 T to 0.9 T, a rotational speed of the top motor ranges from 45 r/min to 75 r/min, and the motor shaft rotates counterclockwise.

The bottom rotating magnet includes a bottom motor, a bottom turntable is disposed on an output shaft of the bottom motor, a fixed frame is disposed on the bottom turntable, and a plurality of bottom rotating permanent magnets are disposed on the fixed frame.

Four bottom rotating permanent magnets are provided, the four bottom rotating permanent magnets are disposed on the bottom turntable at equal angles, each rotating permanent magnet is 20 cm away from a rotation center, an S pole of the rotating permanent magnet points at the seat, a total field strength of the four rotating permanent magnets ranges from 1.2 T to 1.6 T, a rotational speed of the bottom motor ranges from 90 r/min to 180 r/min, and the output shaft rotates clockwise.

An even number of shielding plate permanent magnets of the triangular shielding plate are provided, 10 to 30 shielding plate permanent magnets are provided and are uniformly distributed in pairs, an N pole is disposed on the triangular shielding plate, and a total field strength of the shielding plate permanent magnets on a single triangular shielding plate ranges from 1.2 T to 1.6 T.

The variable electromagnets have a field strength ranging from 0.5 T to 1.0 T and a frequency ranging from 1000 Hz to 3000 Hz.

The triangular shielding plate is an isosceles triangle.

The support frame is a 304 steel support frame, and the triangular shielding plate is a 304 steel or 20-μm galvanized 304 steel plate.

The seat is a wooden seat.

Compared with the prior art, in the present invention, shielding plate permanent magnets are disposed on inner surfaces of three triangular shielding plates forming a pyramid shape, to form a stable magnetic field in the triangular shielding plates. A top rotating magnet is disposed at a top of the triangular shielding plates. A bottom rotating magnet is disposed below a seat. The magnetic field in the triangular shielding plates is rotated, to enable a vortex in turbulence of magnetic lines of force to generate a torsion field. The torque of the torsion field changes the spin states of electrons and atomic cores in a hypoxic microfield in the body of a patient, to arrange the electrons and atomic cores in a uniform magnetic field direction. The magnetic actuation of the electrons and atomic cores can make the microfield environment serialized and orderly and increase the negentropy. In the present invention, the in vivo microcirculation is improved by using a torsion field, so that the number of red blood cells in blood vessels around cancer cells can be increased, the oxygen content around cancer cells can be increased, and the anaerobic metabolism of cancer cells can be inhibited, thereby inhibiting the proliferation of cancer cells.

Where: 1. triangular shielding plate, 2. support frame, 3. permanent magnet, 4. top rotating magnet, 5. bottom rotating magnet, 6. variable electromagnet, 7. seat, 4-1. top motor, 4-2. motor shaft, 4-3. top turntable, 4-4. top rotating permanent magnet, 5-1. bottom motor, 5-2. output shaft, 5-3. bottom turntable, 5-4. fixed frame, and 5-5. bottom rotating permanent magnet.

DESCRIPTION OF THE EMBODIMENTS

The present invention is further described below with reference to the accompanying drawings.

Figure 1:
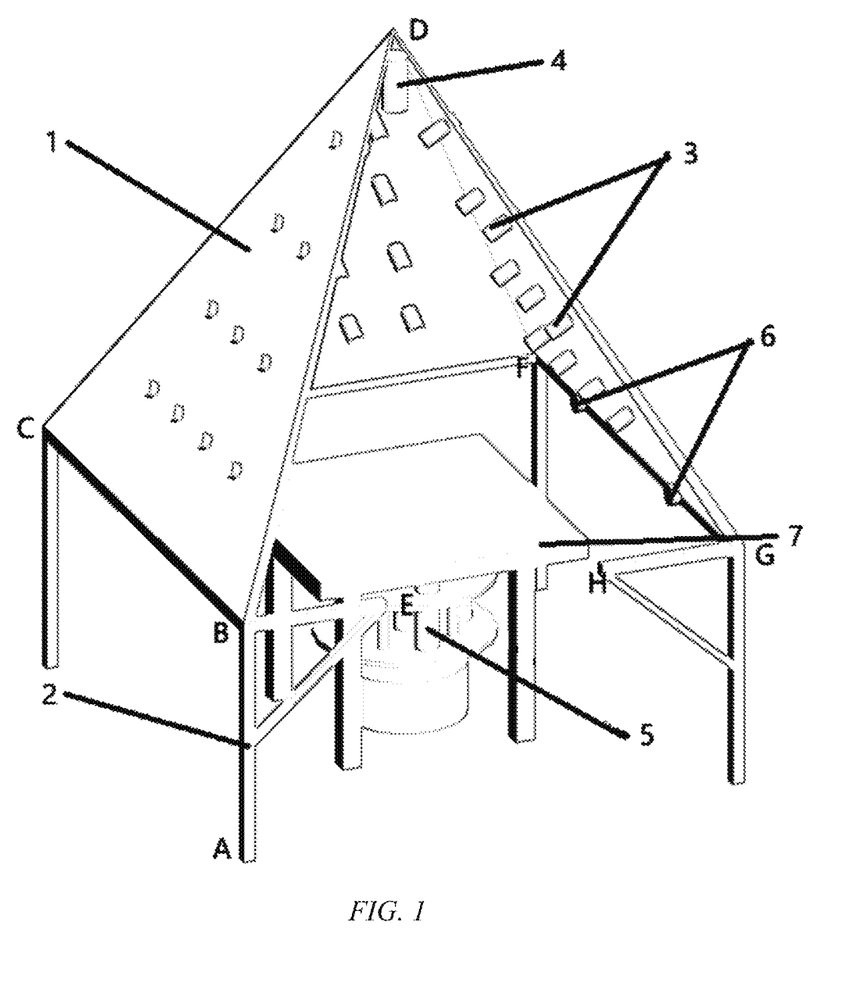
FIG. 1 is a schematic structural diagram according to the present invention.
Figure 2:
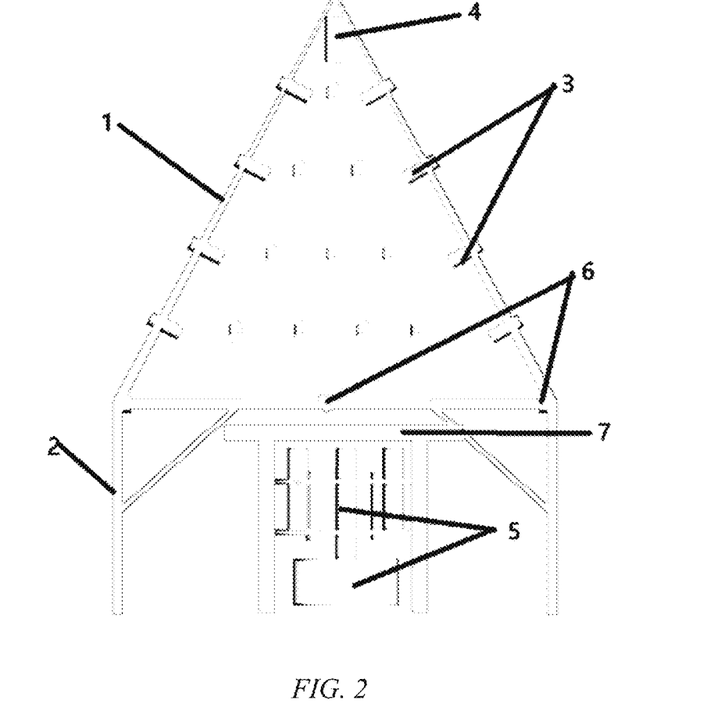
FIG. 2 is a front view according to the present invention.
Figure 3:
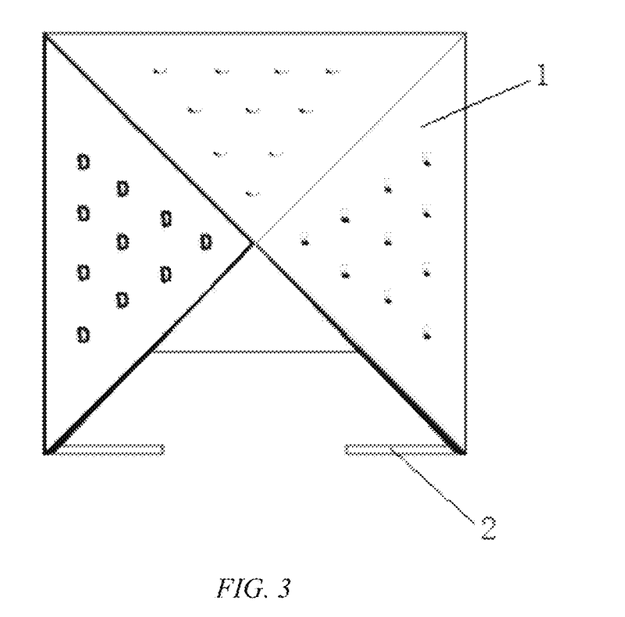
FIG. 3 is a top view according to the present invention.

Referring to FIG. 1, FIG. 2, and FIG. 3, the present invention includes a support frame 2. The support frame 2 is a cuboid. Three triangular shielding plates 1 are disposed on the support frame 2. Bottoms of the triangular shielding plates 1 are disposed on the support frame 2. Adjacent sides of the three triangular shielding plates 1 are connected. The three triangular shielding plates 1 form a pyramid shape. A plurality of shielding plate permanent magnets 3 are disposed on an inner surface of each triangular shielding plate 1. A top rotating magnet 4 is disposed at a top of the three triangular shielding plates 1. A seat 7 is disposed in the support frame 2. A bottom rotating magnet 5 is disposed below the seat 7. The seat 7 is made of a non-magnetically conductive material. Variable electromagnets 6 are disposed on a top frame of the support frame 2. An even number of shielding plate permanent magnets 3 of the triangular shielding plate 1 are provided. 10 to 30 shielding plate permanent magnets 3 are provided and are uniformly distributed in pairs. An N pole is disposed on the triangular shielding plate 1. A total field strength of the shielding plate permanent magnets 3 on a single triangular shielding plate 1 ranges from 1.2 T to 1.6 T. The variable electromagnets 6 have a field strength ranging from 0.5 T to 1.0 T and a frequency ranging from 1000 Hz to 3000 Hz.

Figure 4:
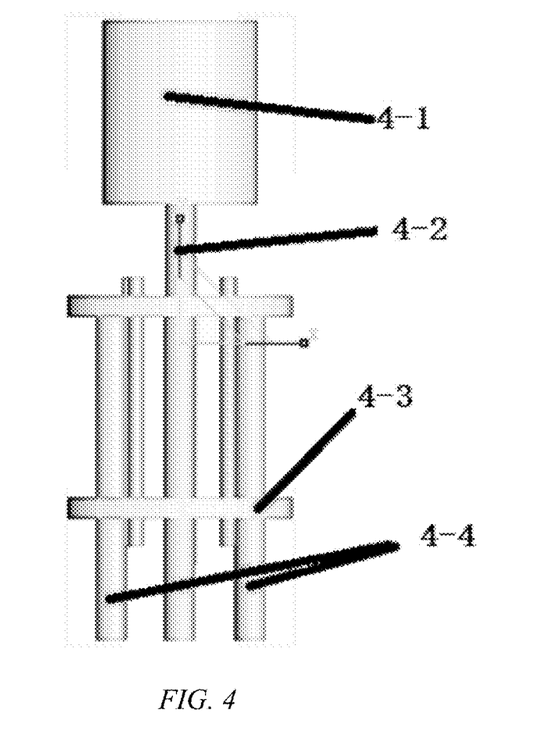
FIG. 4 is a schematic diagram of a top rotating magnet according to the present invention.

Referring to FIG. 4, the top rotating magnet 4 includes a top motor 4-1. A top turntable 4-3 is disposed on a motor shaft 4-2 of the top motor 4-1. A plurality of top rotating permanent magnets 4-4 are disposed on the top turntable 4-3. Four rotating permanent magnets 4-4 are provided. The four rotating permanent magnets 4-4 are disposed on the top turntable 4-3 at equal angles. An S pole of each rotating permanent magnet 4-4 points at the seat 7. The rotating permanent magnet 4-4 is 5 cm away from a rotation center. A total field strength of the four rotating permanent magnets 4-4 ranges from 0.7 T to 0.9 T. A rotational speed of the top motor 4-1 ranges from 45 r/min to 75 r/min. The motor shaft 4-2 rotates counterclockwise.

Figure 5:
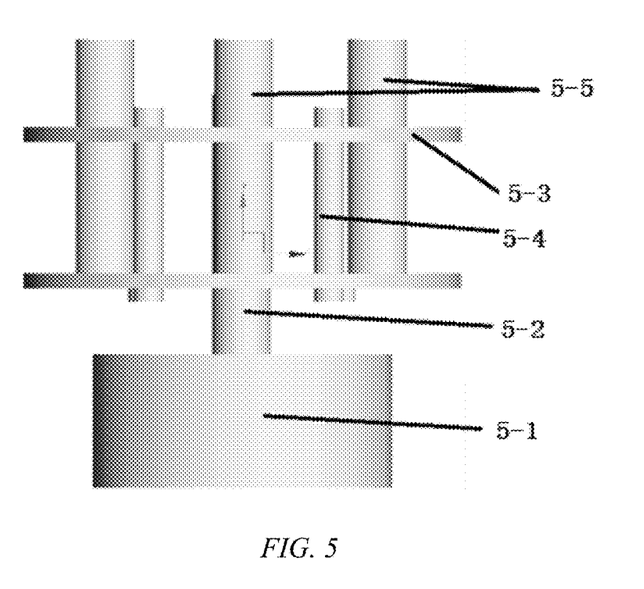
FIG. 5 is a schematic diagram of a bottom rotating magnet according to the present invention.

Referring to FIG. 5, the bottom rotating magnet 5 includes a bottom motor 5-1. A bottom turntable 5-3 is disposed on an output shaft 5-2 of the bottom motor 5-1. A fixed frame is disposed on the bottom turntable 5-3. A plurality of bottom rotating permanent magnets are disposed on the fixed frame 5-4. Four bottom rotating permanent magnets 5-5 are provided. The four bottom rotating permanent magnets 5-5 are disposed on the bottom turntable 5-3 at equal angles. Each rotating permanent magnet 5-5 is 20 cm away from a rotation center. An S pole of the rotating permanent magnet 5-5 points at the seat 7. A total field strength of the four rotating permanent magnets 5-5 ranges from 1.2 T to 1.6 T. A rotational speed of the bottom motor 5-1 ranges from 90 r/min to 180 r/min. The output shaft 5-2 rotates clockwise.

Preferably, the support frame 2 is formed by welding four 60-cm long, three 130-cm long, two 40-cm long, two 50-cm long, and four 146-cm long hollow square bars with a cross-sectional size of 3 cm*3 cm.

Preferably, the triangular shielding plate 1 is an isosceles triangle.

Preferably, the support frame 2 is a 304 steel support frame, and the triangular shielding plate 1 is a 304 steel or 20-μm galvanized 304 steel plate.

Preferably, the seat 7 is a wooden seat with a height of 50 cm, and a side length of a seat surface is 50 cm.

Preferably, referring to FIG. 1, the variable electromagnets 6 are distributed on five sides BC, BE, CF, FG, and GH of the framework of the hollow square bars.

In the present invention, the magnetic field is rotated, to enable a vortex in turbulence of magnetic lines of force to generate a torsion field. The torque of the torsion field changes the spin states of electrons and atomic cores in a hypoxic microfield in the body of a patient, to arrange the electrons and atomic cores in a uniform magnetic field direction. The magnetic actuation of the electrons and atomic cores can make the microfield environment serialized and orderly and increase the negentropy. Due to the vibration of iron cores in hemoglobin molecules, hemoglobin is activated, the movement rates of red blood cells are increased, and the amount of oxygen supply is increased. In addition, out-of-order cancer cells are arranged in order to promote angiogenic dormancy. As the topology of the magnetic field changes constantly, laminar flows of magnetic lines of force are distorted, twisted, coupled, and superimposed, making fluids and red blood cells in the human body oscillate to increase the movement rates, to accelerate the metabolism of the circulatory system, the digestive system, and the lymphatic system, thereby improving the disease resistance of patients and enhancing the quality of life of patients.

Case 1:

Case 1 is a 63-year-old female diagnosed with HER-2 (HR positive) breast cancer according to the first examination result in July 2018 (see Table 1). In the period from August 2018 to March 2019, the patient was treated with six cycles of treatment with the pyramid energy cabin (see Table 2 for the settings of treatment parameters). Each cycle of treatment includes two treatments. An MRI test and a carcinoembryonic antigen test were performed respectively after the third cycle of treatment and the sixth cycle of treatment were completed. MRI and carcinoembryonic antigen test results of the three examinations (Table 3) showed that after the patient had been treated with the six cycles of treatment, the size of the tumor of the patient had not increased significantly, there was no increase in the carcinoembryonic antigen value, and no metastasis of tumor cells was found during the treatment. The tumor was excised after the sixth cycle of treatment. After the surgery, the patient was treated with four cycles of treatment with the pyramid energy cabin. The patient is now fully recovered.

TABLE 1

Test results of immunohistochemical indicators of breast cancer of Case 1

| Immunohistochemical indicator | Estrogen receptor (ER) | Progesterone receptor (PR) | Her-2 protein | Ki67 (proliferation indicator) | P63 |
|---|---|---|---|---|---|
| Test result | – | – | +++ | 40% | Missing |

TABLE 2

Treatment parameters of the pyramid energy cabin of Case 1

| Cycle of treatment | Field strength of shielding plate permanent magnets | Top field strength | | Bottom field strength | | Variable electromagnet | | Treatment time |
|---|---|---|---|---|---|---|---|---|
| | | Field strength | Revolutions | Field strength | Revolutions | Field strength | Frequency | |
| 1 | 1.2 | 0.7 | 45 | 1.2 | 90  | 0.5 | 1000 Hz | 60 min |
| 2 | 1.4 | 0.8 | 60 | 1.4 | 120 | 0.7 | 2000 Hz | 60 min |
| 3 | 1.6 | 0.9 | 75 | 1.6 | 150 | 1.0 | 3000 Hz | 30 min |
| 4 | 1.4 | 0.8 | 60 | 1.4 | 120 | 0.7 | 2000 Hz | 60 min |
| 5 | 1.4 | 0.7 | 60 | 1.4 | 120 | 0.5 | 2000 Hz | 60 min |
| 6 | 1.4 | 0.7 | 60 | 1.4 | 120 | 0.5 | 2000 Hz | 60 min |

TABLE 3

Results of three times of MRI and carcinoembryonic antigen tests before and during the treatment

| Examination Time | Test Indicator | | Notes |
|---|---|---|---|
| | MR (left breast lump) | Carcinoembryonic antigen (CEA) (0 ng/ml to 5 ng/mL) | |
| Jul. 16, 2018 | 48 mm*61 mm | 13.75 | Examination results before the treatment |
| Oct. 26, 2018 | 44 mm*53 mm | 11.9 | Examination results after the third cycle of treatment |
| Mar. 28, 2019 | 48 mm*58 mm | 12.84 | Examination results after the sixth cycle of treatment |

Case 2:

Case 2 is a 47-year-old female found with hyperplasia in the left breast in August 2016. The size of the lump was 17 mm*33 mm and was not treated. The case was confirmed with breast cancer in another examination (MRI) in October 2017. The size of the lump was 21 mm*39 mm. The lump grew and was dense. An immunological treatment with melittin was performed. In the MRI reexamination in August 2018, the size of the lump was 22 mm*37 mm. From September 2018 to December 2018, the patient was treated with three cycles of treatment (see Table 4 for the settings of treatment parameters). Each cycle of treatment includes two treatments. The patient was reexamined after three cycles of treatment (results are shown in Table 5). The sizes of the lump in the MRI results were respectively 20 mm*35 mm, 18 mm*31 mm, and 12 mm*25 mm. The condition of the patient had improved after the three cycles of treatment and had gradually recovered.

TABLE 4

Treatment parameters of the pyramid energy cabin of Case 2

| Cycle of treatment | Field strength of shielding plate permanent magnets | Top field strength | | Bottom field strength | | Variable electromagnet | | Treatment time |
|---|---|---|---|---|---|---|---|---|
| | | Field strength | Revolutions | Field strength | Revolutions | Field strength | Frequency | |
| 1 | 1.2 | 0.7 | 45 | 1.2 | 90  | 0.5 | 1000 Hz | 60 min |
| 2 | 1.2 | 0.8 | 60 | 1.4 | 120 | 0.7 | 2000 Hz | 90 min |
| 3 | 1.2 | 0.8 | 60 | 1.2 | 120 | 0.7 | 2000 Hz | 90 min |

TABLE 5

Results of six times of MRI and carcinoembryonic antigen tests before and during the treatment

| | Test indicator | | |
|---|---|---|---|
| Test time | Size of the left breast lump | Carcinoembryonic antigen (CEA) (0 ng/mL to 5 ng/ml) | Notes |
| Aug. 30, 2016 | 17 mm*33 mm | 6.32 | Initial examination |
| Oct. 27, 2017 | 21 mm*39 mm | 7.92 | Reexamination |
| Aug. 2, 2018 | 22 mm*37 mm | 10.32 | Reexamination after the immunological treatment with melittin |
| Oct. 15, 2018 | 20 mm*35 mm | 6.69 | Reexamination after the first cycle of treatment |
| Dec. 29, 2018 | 18 mm*31 mm | 6.01 | Reexamination after the second cycle of treatment |
| Apr. 21, 2019 | 12 mm*25 mm | 5.02 | Reexamination after the third cycle of treatment |

Figure 6:
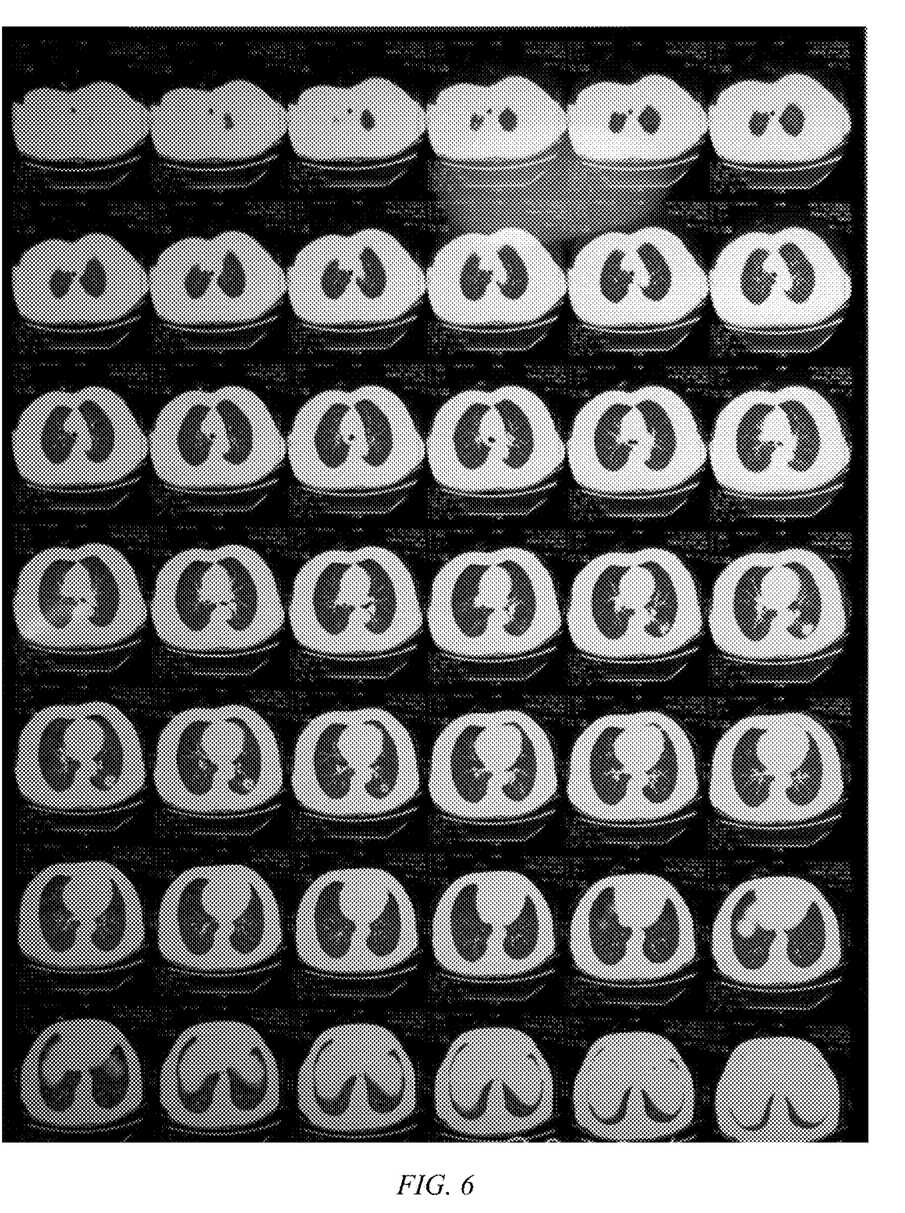
FIG. 6 is a CT image of Case 3 after the first cycle of treatment.
Figure 7:
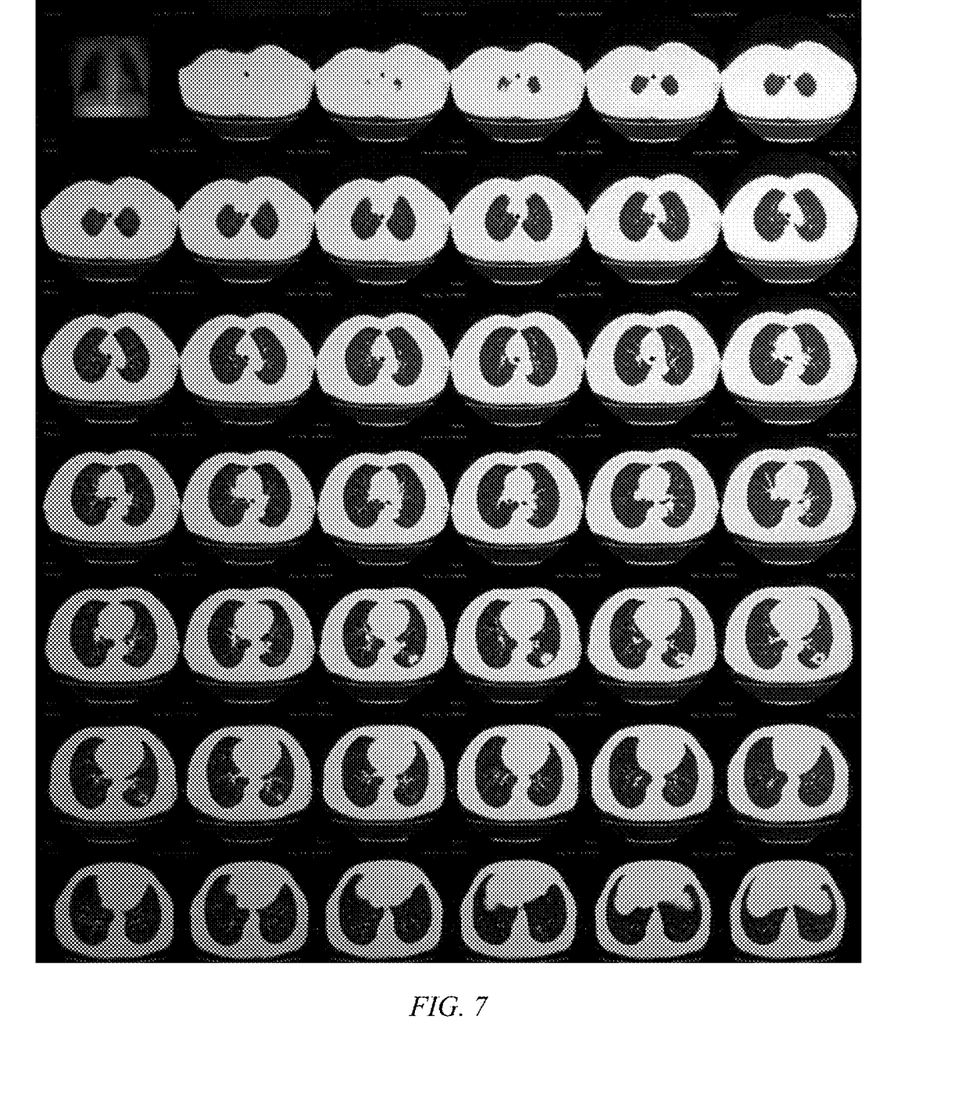
FIG. 7 is a CT image of Case 3 after the fifth cycle of treatment.

Case 3:

Case 3 is a 63-year-old female found with nodules in the left lower lobe and formation of thick-walled cavities according to test results in October 2018, indicating a high possibility of peripheral lung cancer. Multiple lymph node shadows were found in both armpits, with local mild swelling. The patient was treated with the first cycle of treatment in November 2018 (see Table 6 for the settings of treatment parameters), and reexamination was performed in the same month (see Table 7 for the results). Referring to FIG. 6, there was no significant increase in the size of tumor. The patient was then treated with four cycles of treatment. Each cycle of treatment includes two treatments. Second reexamination was performed in March 2019 (see Table 7 for the results). Referring to FIG. 7, the size of the tumor had increased. The CT examination results in April showed that the size of the tumor had decreased. The patient had the surgery in April 10. The tumor did not recur after the surgery.

TABLE 6

Treatment parameters of the pyramid energy cabin of Case 3

| | Field strength of shielding plate | Top field strength | | Bottom field strength | | Variable electromagnet | | |
|---|---|---|---|---|---|---|---|---|
| Cycle of treatment | permanent magnets | Field strength | Revolutions | Field strength | Revolutions | Field strength | Frequency | Treatment time |
| 1 | 1.2 | 0.7 | 45 | 1.2 | 90 | 0.5 | 1000 Hz | 60 min |
| 2 | 1.2 | 0.8 | 60 | 1.2 | 120 | 0.7 | 2000 Hz | 60 min |
| 3 | 1.2 | 0.9 | 60 | 1.2 | 120 | 0.9 | 1000 Hz | 60 min |
| 4 | 1.2 | 0.8 | 60 | 1.2 | 120 | 0.7 | 1000 Hz | 90 min |
| 5 | 1.2 | 0.8 | 60 | 1.2 | 120 | 0.7 | 1000 Hz | 90 min |

TABLE 7

Results of four times of CT examination, carcinoembryonic antigen, and bilateral axillary lymph node visualization tests before and during the treatment

| | Test indicator | | | |
|---|---|---|---|---|
| Test time | CT (lump in the left lung) | Carcinoembryonic antigen (CEA) (0 ng/ml to 3.4 ng/ml) | Bilateral axillary lymph node visualization | Notes |
| Oct. 17, 2018 | 26 mm*22 mm*24 mm | 1.610 | 13 mm*8 mm | Examination results before the treatment |
| Nov. 26, 2018 | 26 mm*22 mm*24 mm | 1.628 | 13 mm*8 mm | Examination results after the first cycle of treatment |
| Mar. 26, 2019 | 38 mm*31 mm*30 mm | 3.729 | 15 mm*12 mm | Examination results after the fifth cycle of treatment |

TABLE 7-continued

Results of four times of CT examination, carcinoembryonic antigen, and bilateral axillary lymph node visualization tests before and during the treatment

| | Test indicator | | | |
|---|---|---|---|---|
| Test time | CT (lump in the left lung) | Carcinoembryonic antigen (CEA) (0 ng/ml to 3.4 ng/ml) | Bilateral axillary lymph node visualization | Notes |
| Apr. 1, 2019 | 36 mm*28 mm*32 mm | 2.824 | 17 mm*13 mm | Examination results before the surgery |

Figure 8:
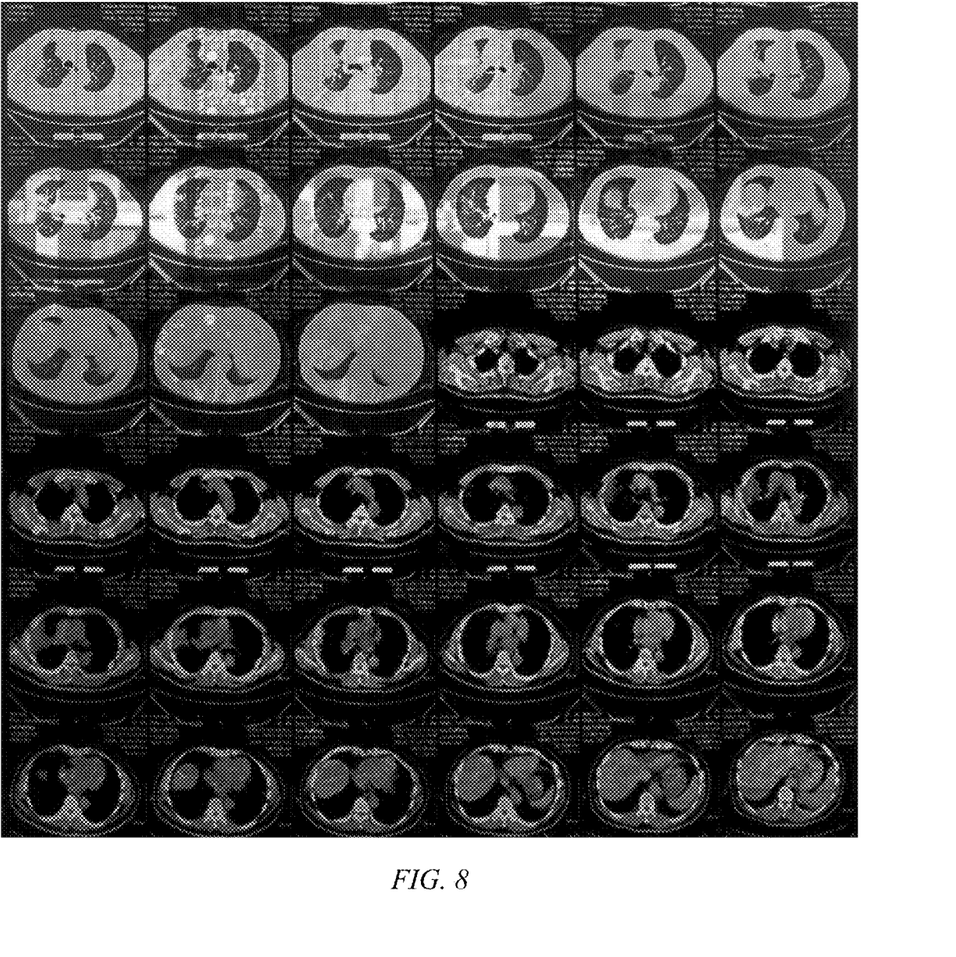
FIG. 8 is a CT image of Case 4 after the eighth cycle of treatment.
Figure 9:
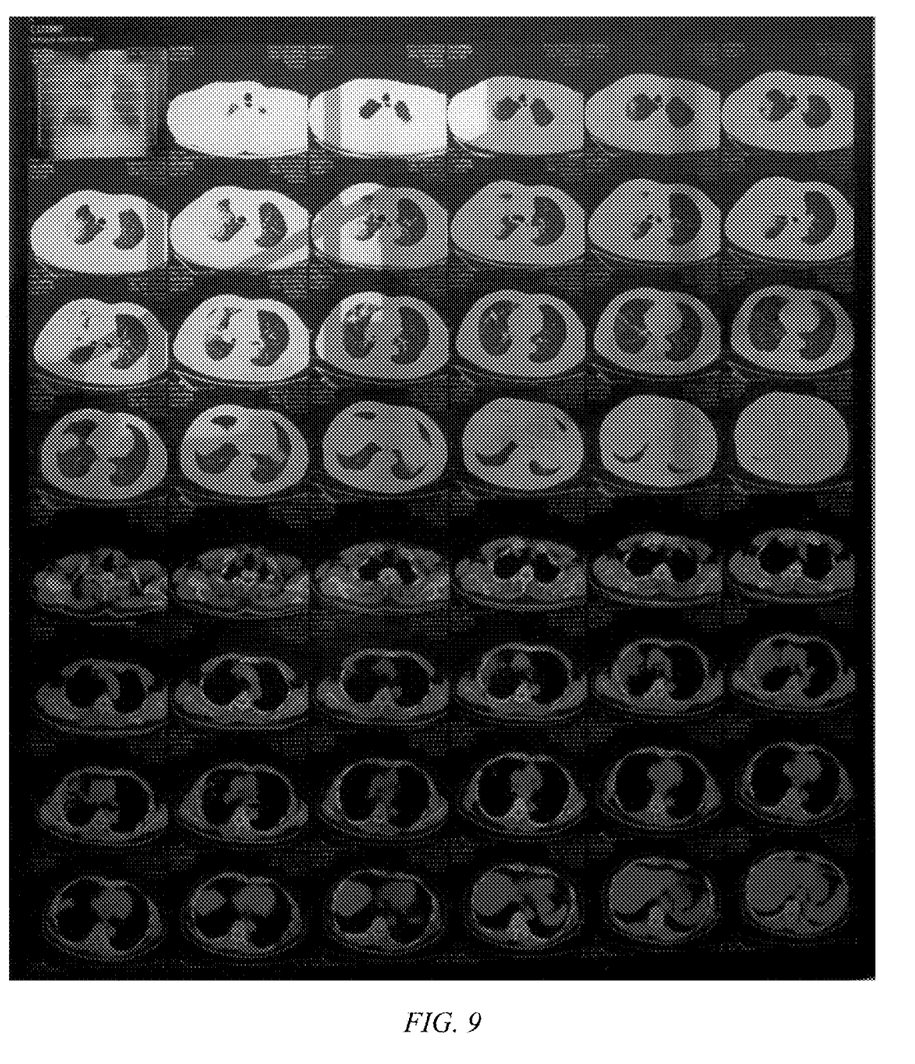
FIG. 9 is a CT image of Case 4 after the eleventh cycle of treatment.

Case 4:

Case 4 is a 58-year-old male confirmed with lung cancer (left lung) with well-differentiated mucinous adenocarcinoma of lung in 2013. (T3N0M0, stage Ma). Cancer cells were brought under control after surgery and chemotherapy. Four years later, intrapulmonary metastasis occurred in 2017. Chemotherapy, radiotherapy, and Chinese traditional treatment showed no therapeutic efficacy. In a CT test in November 2018, multiple nodules were found in the right lung. Ground-glass high-density shadows were seen at the edge of some lesions. From December 2018 to January 2019, the patient was treated with two cycles of treatment (see Table 8 for the settings of treatment parameters). Each cycle of treatment includes two treatments. In a CT test in February 2019, visible high-density nodule shadows were significantly reduced in size in the right middle lung lobe region. Compared with the previous test, the inflammatory part had been absorbed and had a reduced range. The reexamination in March 2019 proved that the CT test result in February 2019 was correct. Six cycles of treatment were then performed. Referring to FIG. 8, in the reexamination in November 2109, there was no increase in the range of the visible high-density nodule shadows in the right middle lung lobe region. There was no significant change in the range of consolidation of inflammation. The patient stopped the treatment after three more cycles of treatment. Referring to FIG. 9, the cancer had not recurred within two years.

TABLE 9

Results of five times of CT examination, carcinoembryonic antigen test, and inflammatory status before and during the treatment

| | Test indicator | | |
|---|---|---|---|
| Test time | CT (Visible high-density nodule shadows in the right middle lung lobe region) | Carcinoembryonic antigen (CEA) (0 ng/ml to 3.4 ng/mL) | Notes |
| Nov. 27, 2018 | 57 mm*32 mm | 4.671 | Examination results before the treatment |
| Feb. 15, 2019 | 12 mm*17 mm | 3.317 | Examination results after the second cycle of treatment |
| Mar. 19, 2019 | 10.5 mm*10.5 mm | 3.520 | Examination results after the second cycle of treatment |
| Nov. 5, 2019 | 10.5 mm*10.5 mm | 2.736 | Examination results after the eighth cycle of treatment |
| Mar. 7, 2020 | 10.6 mm*10.9 mm | 3.081 | Examination results after the eleventh cycle of treatment |

As can be seen from the foregoing treatment cases, the rotating negative (S pole) magnetic field-variable pyramid energy cabin can effectively inhibit the metastasis of cancer

TABLE 8

Treatment parameters of the pyramid energy cabin of Case 4

| Cycle of treatment | Field strength of shielding plate permanent magnets | Top field strength Field strength | Top field strength Revolutions | Bottom field strength Field strength | Bottom field strength Revolutions | Variable electromagnet Field strength | Variable electromagnet Frequency | Treatment time |
|---|---|---|---|---|---|---|---|---|
| 1 | 1.2 | 0.7 | 45 | 1.2 | 90 | 0.5 | 1000 Hz | 60 min |
| 2 | 1.4 | 0.8 | 60 | 1.4 | 120 | 0.7 | 1000 Hz | 60 min |
| 3 | 1.6 | 0.9 | 75 | 1.6 | 150 | 1.0 | 1000 Hz | 30 min |
| 4 | 1.4 | 0.8 | 60 | 1.2 | 120 | 0.7 | 1000 Hz | 60 min |
| 5 | 1.2 | 0.8 | 60 | 1.2 | 120 | 0.7 | 1000 Hz | 60 min |
| 6 | 1.2 | 0.8 | 60 | 1.2 | 120 | 0.7 | 1000 Hz | 60 min |
| 7 | 1.2 | 0.8 | 60 | 1.2 | 120 | 0.7 | 1000 Hz | 60 min |
| 8 | 1.2 | 0.8 | 60 | 1.2 | 120 | 0.7 | 1000 Hz | 60 min |
| 9 | 1.2 | 0.8 | 60 | 1.2 | 120 | 0.7 | 1000 Hz | 60 min |
| 10 | 1.2 | 0.8 | 60 | 1.2 | 120 | 0.7 | 1000 Hz | 60 min |
| 11 | 1.2 | 0.8 | 60 | 1.2 | 120 | 0.7 | 1000 Hz | 60 min | cells and an increase in the volume of a tumor before surgery and help patients to recover faster after surgery through collaborative treatment with surgery during the treatment of patients with middle and late stages of breast cancer. During the treatment of patients with an early stage of breast cancer, through multiple cycles of treatment, the volume of a tumor can gradually reduce, surrounding tissue can restore, and eventually the patients can be cured. During the treatment of patients with lung cancer with the rotating negative (S pole) magnetic field-variable pyramid energy cabin, through cooperation with measures such as surgery, radiotherapy, and chemotherapy, the metastasis of cancer cells and an increase in the volume of a tumor can be effectively controlled, and side effects of radiotherapy and chemotherapy can be mitigated and eliminated, thereby enhancing the quality of life of patients.

In the process of assisting cancer treatment using the rotating negative (S pole) magnetic field-variable pyramid energy cabin, the metastasis of cancer cells and an increase in the volume of a tumor can be inhibited, and the expression of carcinoembryonic antigens (CEA) tends to be stable, so that the quality of life of patients and the survival of patients can be increased.

The present invention can regulate the in vivo microcirculation to assist in the treatment of cancers, including lung, breast, stomach, colorectal, liver, esophagus, thyroid, endometrial, brain, and pancreatic cancers.

What is claimed is:

1. A rotating magnetic field-variable pyramid energy cabin, comprising a support frame (2), wherein the support frame (2) is a cuboid, three triangular shielding plates (1) are disposed on the support frame (2), bottoms of the triangular shielding plates (1) are disposed on the support frame (2), adjacent sides of the three triangular shielding plates (1) are connected, the three triangular shielding plates (1) form a pyramid shape, a plurality of shielding plate permanent magnets (3) are disposed on an inner surface of each triangular shielding plate (1), a top rotating magnet (4) is disposed at a top of the three triangular shielding plates (1), a seat (7) is disposed in the support frame (2), a bottom rotating magnet (5) is disposed below the seat (7), the seat (7) is made of a non-magnetically conductive material, and variable electromagnets (6) are disposed on a top frame of the support frame (2).

2. The rotating magnetic field-variable pyramid energy cabin according to claim 1, wherein the top rotating magnet (4) comprises a top motor (4-1), a top turntable (4-3) is disposed on a motor shaft (4-2) of the top motor (4-1), and a plurality of top rotating permanent magnets (4-4) are disposed on the top turntable (4-3).

3. The rotating magnetic field-variable pyramid energy cabin according to claim 2, wherein four rotating permanent magnets (4-4) are provided, the four rotating permanent magnets (4-4) are disposed on the top turntable (4-3) at equal angles, an S pole of each rotating permanent magnet (4-4) points at the seat (7), the rotating permanent magnet (4-4) is 5 cm away from a rotation center, a total field strength of the four rotating permanent magnets (4-4) ranges from 0.7 T to 0.9 T, a rotational speed of the top motor (4-1) ranges from 45 r/min to 75 r/min, and the motor shaft (4-2) rotates counterclockwise.

4. The rotating magnetic field-variable pyramid energy cabin according to claim 1, wherein the bottom rotating magnet (5) comprises a bottom motor (5-1), a bottom turntable (5-3) is disposed on an output shaft (5-2) of the bottom motor (5-1), a fixed frame (5-4) is disposed on the bottom turntable (5-3), and a plurality of bottom rotating permanent magnets (5-5) are disposed on the fixed frame (5-4).

5. The rotating magnetic field-variable pyramid energy cabin according to claim 4, wherein four bottom rotating permanent magnets (5-5) are provided, the four bottom rotating permanent magnets (5-5) are disposed on the bottom turntable (5-3) at equal angles, each rotating permanent magnet (5-5) is 20 cm away from a rotation center, an S pole of the rotating permanent magnet (5-5) points at the seat (7), a total field strength of the four rotating permanent magnets (5-5) ranges from 1.2 T to 1.6 T, a rotational speed of the bottom motor (5-1) ranges from 90 r/min to 180 r/min, and the output shaft (5-2) rotates clockwise.

6. The rotating magnetic field-variable pyramid energy cabin according to claim 1, wherein an even number of shielding plate permanent magnets (3) of the triangular shielding plate (1) are provided, 10 to 30 shielding plate permanent magnets (3) are provided and are uniformly distributed in pairs, an N pole is disposed on the triangular shielding plate (1), and a total field strength of the shielding plate permanent magnets (3) on a single triangular shielding plate (1) ranges from 1.2 T to 1.6 T.

7. The rotating magnetic field-variable pyramid energy cabin according to claim 1, wherein the variable electromagnets (6) have a field strength ranging from 0.5 T to 1.0 T and a frequency ranging from 1000 Hz to 3000 Hz.

8. The rotating magnetic field-variable pyramid energy cabin according to claim 1, wherein the triangular shielding plate (1) is an isosceles triangle.

9. The rotating magnetic field-variable pyramid energy cabin according to claim 1, wherein the support frame (2) is a 304 steel support frame, and the triangular shielding plate (1) is a 304 steel or 20-μm galvanized 304 steel plate.

10. The rotating magnetic field-variable pyramid energy cabin according to claim 1, wherein the seat (7) is a wooden seat.

* * * * *